United States Patent
Adachi et al.

(10) Patent No.: US 10,132,939 B2
(45) Date of Patent: Nov. 20, 2018

(54) SCINTILLATOR, SCINTILLATOR ARRAY, RADIATION DETECTOR, AND RADIATION EXAMINATION DEVICE

(71) Applicants: KABUSHIKI KAISHA TOSHIBA, Tokyo (JP); TOSHIBA MATERIALS CO., LTD., Yokohama-Shi (JP)

(72) Inventors: Yoshitaka Adachi, Yokohama (JP); Akihisa Saito, Yokohama (JP); Masaki Toyoshima, Fujisawa (JP); Eiji Oyaizu, Yokohama (JP); Kazumitsu Morimoto, Fujisawa (JP); Takashi Rokutanda, Yokohama (JP)

(73) Assignees: Kabushiki Kaisha Toshiba, Minato-Ku (JP); Toshiba Materials Co., Ltd., Yokohama-Shi (JP)

( * ) Notice: Subject to any disclaimer, the term of this patent is extended or adjusted under 35 U.S.C. 154(b) by 24 days.

(21) Appl. No.: 15/450,641

(22) Filed: Mar. 6, 2017

(65) Prior Publication Data
US 2017/0199285 A1 Jul. 13, 2017

Related U.S. Application Data

(63) Continuation of application No. PCT/JP2015/004853, filed on Sep. 24, 2015.

(30) Foreign Application Priority Data

Sep. 25, 2014 (JP) ................................. 2014-195606

(51) Int. Cl.
*G01T 1/20* (2006.01)
*C09K 11/77* (2006.01)
(Continued)

(52) U.S. Cl.
CPC ........ *G01T 1/2018* (2013.01); *C09K 11/7771* (2013.01); *A61B 6/03* (2013.01); *G01N 23/04* (2013.01)

(58) Field of Classification Search
CPC .................................................... G01T 1/2018
See application file for complete search history.

(56) References Cited

U.S. PATENT DOCUMENTS 4,525,628 A * 6/1985 DiBianca ................ C04B 35/50
250/361 R
5,302,817 A 4/1994 Yokota et al.
(Continued)

FOREIGN PATENT DOCUMENTS

EP 1550885 A1 * 7/2005 ......... C09K 11/7767
JP 62-045682 A1 2/1987
(Continued)

OTHER PUBLICATIONS

International Search Report and Written Opinion (Application No. PCT/JP2015/004853) dated Dec. 15, 2015.
(Continued)

*Primary Examiner* — Marcus Taningco
*Assistant Examiner* — Djura Malevic
(74) *Attorney, Agent, or Firm* — Burr & Brown, PLLC (57) ABSTRACT

To suppress a decrease in optical output of a scintillator. A scintillator includes a sintered body of 1 mm$^3$ or less that contains a rare earth oxysulfide. In a composition image obtained by observing a cross-section of the sintered body under a scanning electron microscope, the sum of the number of oxide regions that contain at least one of a rare earth oxide different from the rare earth oxysulfide and an impurity metal oxide and the number of sulfide regions that contain at least one of a rare earth sulfide different from the rare earth oxysulfide and an impurity metal sulfide, which
(Continued)

exist in a unit area of 500 µm×500 µm, is zero or more and five or less. Each of the oxide regions and the sulfide regions has a major axis of zero or more and 100 µm or less.

10 Claims, 3 Drawing Sheets (51) Int. Cl.
A61B 6/03 (2006.01)
G01N 23/04 (2018.01)

(56) References Cited

U.S. PATENT DOCUMENTS

| | | | | |
|---|---|---|---|---|
| 5,521,387 | A * | 5/1996 | Riedner | C04B 35/50 264/654 250/367 |
| 6,384,417 | B1 * | 5/2002 | Okumura | G01T 1/20 250/367 |
| 6,504,156 | B1 * | 1/2003 | Takahara | C09K 11/7771 250/361 R |
| 6,630,077 | B2 * | 10/2003 | Shiang | G01T 1/2023 250/363.04 |
| 6,630,675 | B2 * | 10/2003 | Ghelmansarai | C09K 11/7771 250/366 |
| 7,094,362 | B2 * | 8/2006 | Setlur | C09K 11/7774 252/301.4 F |
| 7,230,248 | B2 * | 6/2007 | Fukuta | C04B 35/547 250/370.11 |
| 8,083,968 | B2 * | 12/2011 | Fukuta | C09K 11/7769 250/390.11 |
| 8,937,286 | B2 * | 1/2015 | Morimoto | G21K 4/00 250/363.01 |
| 9,217,794 | B2 * | 12/2015 | Morimoto | G01N 23/046 |
| 9,771,515 | B2 * | 9/2017 | Wang | C09K 11/7771 |
| 2003/0127630 | A1 * | 7/2003 | Vartuli | G01T 1/2023 252/301.4 R |
| 2004/0100000 | A1 * | 5/2004 | Kobusch | C04B 35/50 264/654 |
| 2006/0054830 | A1 | 3/2006 | Oyaizu et al. | |
| 2006/0145085 | A1 * | 7/2006 | Fukuta | C04B 35/547 250/370.11 |
| 2007/0027025 | A1 * | 2/2007 | LaCourse | C04B 35/547 501/152 |
| 2008/0210885 | A1 * | 9/2008 | Bolyasnikova | C04B 35/547 250/473.1 |
| 2010/0294939 | A1 * | 11/2010 | Kuntz | C04B 35/01 250/361 R |
| 2011/0303873 | A1 * | 12/2011 | Fukuta | C01G 19/006 252/301.4 R |
| 2012/0012787 | A1 * | 1/2012 | LaCourse | C09K 11/7701 252/301.4 R |
| 2012/0145962 | A1 * | 6/2012 | Fukuta | C09K 11/7774 252/301.4 R |
| 2012/0241627 | A1 * | 9/2012 | Noda | G01T 1/202 250/361 R |
| 2014/0301527 | A1 * | 10/2014 | Morimoto | G01N 23/046 378/4 |
| 2016/0282480 | A1 * | 9/2016 | Yamamoto | G21K 4/00 |

FOREIGN PATENT DOCUMENTS

| | | |
|---|---|---|
| JP | 2928677 B2 | 8/1999 |
| JP | 2001-131546 A1 | 5/2001 |
| JP | 4959877 B2 | 6/2012 |
| JP | 2012-187137 A1 | 10/2012 |
| WO | 2004/029657 A1 | 4/2004 |
| WO | 2013/080565 A1 | 6/2013 |

OTHER PUBLICATIONS

Extended European Search Report, European Application No. 15843514.9, dated Mar. 28, 2018 (6 pages).

* cited by examiner

SCINTILLATOR, SCINTILLATOR ARRAY, RADIATION DETECTOR, AND RADIATION EXAMINATION DEVICE

CROSS-REFERENCE TO RELATED APPLICATIONS

This application is a continuation of prior International Application No. PCT/JP2015/004853, filed on Sep. 24, 2015 which is based upon and claims the benefit of priority from Japanese Patent Application No. 2014-195606, filed on Sep. 25, 2014; the entire contents of all of which are incorporated herein by reference.

FIELD

Embodiments described herein generally relate to a scintillator, a scintillator array, a radiation detector, and a radiation examination device.

BACKGROUND

Radiation examination devices such as an X-ray CT (Computed Tomography: CT) device have been used for various applications including medical use, industrial use, and so on. As the radiation examination device, for example, a multi-slice X-ray CT device having a scintillator array mounted thereon can be cited. The multi-slice X-ray CT device enables overlaying of sliced images and three-dimensional display of a CT image.

The scintillator array has a plurality of detection elements (photodiodes or the like) arranged in a matrix in a plane. Further, a radiation detector to be mounted on the radiation examination device includes a plurality of scintillators provided every single detection element. In the radiation examination device, X-rays entering the scintillators are converted into visible light and the visible light is converted into electrical signals by the detection elements, thereby obtaining an image. In recent years, in order to obtain high resolution, the detection elements are miniaturized to thereby narrow a pitch between the plural detection elements. The size of the scintillator is preferred to be small with miniaturization of the detection element.

As a material of the scintillator, for example, a gadolinium oxysulfide sintered body can be cited. For example, a ceramic scintillator made of the gadolinium oxysulfide sintered body has a fixed color body with chromaticity coordinates (x, y). The chromaticity coordinates are measured by using a color meter, for example. The minimum diameter that can be measured by a general color meter falls within a range of about 2 mm or more to 8 mm or less. A measurement area when the diameter is 2 mm or more and 8 mm or less is, for example, 3.14 $mm^2$ or more and 50.24 $mm^2$ or less. The chromaticity of a measured region is sometimes found to be in an appropriate range within the above-described measurement area range even when minute foreign matters are present.

When the ceramic scintillator is small in size, the effect on emission characteristics is likely to be large even when a slight composition deviation occurs. Therefore, when the composition deviation occurs, an optical output that converts X-rays into visible light sometimes decreases. Further, in a scintillator array including a plurality of ceramic scintillators arranged in a matrix in a plane, the optical output between the ceramic scintillators decreases, and thereby sensitivity as the scintillator array decreases.

SUMMARY

One of the problems to be solved by one aspect of the present invention is to suppress a decrease in optical output of a scintillator array.

A ceramic scintillator according to an embodiment includes a sintered body of 1 $mm^3$ or less that contains a rare earth oxysulfide. In a composition image obtained by observing a cross-section of the sintered body under a scanning electron microscope, the sum of the number of oxide regions that contain at least one of a rare earth oxide different from the rare earth oxysulfide and an impurity metal oxide and the number of sulfide regions that contain at least one of a rare earth sulfide different from the rare earth oxysulfide and an impurity metal sulfide, which exist in a unit area of 500 μm×500 μm, is five or less (including zero). Each of the oxide regions and the sulfide regions has a major axis of 100 μm or less (including zero).

DETAILED DESCRIPTION

Figure 1:
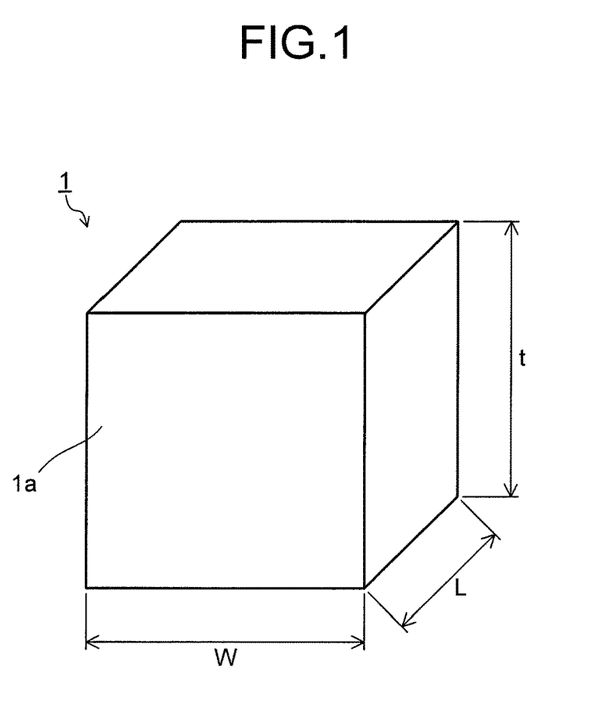
FIG. 1 is a schematic view illustrating a ceramic scintillator according to an embodiment.

FIG. 1 is a schematic view illustrating a ceramic scintillator according to an embodiment. FIG. 1 illustrates a ceramic scintillator 1. The ceramic scintillator 1 includes a rare earth oxysulfide sintered body 1a containing a rare earth oxysulfide. The rare earth oxysulfide sintered body 1a has a volume of 1 $mm^3$ or less.

FIG. 1 illustrates the rare earth oxysulfide sintered body 1a having a cubic body. The embodiment is not limited to this, and the rare earth oxysulfide sintered body 1a may have a rectangular parallelepiped shape, for example. A length L (in the longitudinal direction) of the rare earth oxysulfide sintered body 1a, a width W (in the lateral direction) of the rare earth oxysulfide sintered body 1a, and a thickness t of the rare earth oxysulfide sintered body 1a are each preferred to be 1 mm or less, for example.

In the ceramic scintillator according to the embodiment, the volume of the rare earth oxysulfide sintered body 1a may be 0.72 $mm^3$ or less. At this time, the length L (in the longitudinal direction) of the rare earth oxysulfide sintered body 1a is preferred to be 0.8 mm or less, for example. The width W (in the lateral direction) of the rare earth oxysulfide sintered body 1a is preferred to be 0.9 mm or less, for example. The thickness t of the rare earth oxysulfide sintered body 1a is preferred to be 1 mm or less, for example. Miniaturizing the ceramic scintillator enables an image that is detected in, for example, a radiation examination device to have high definition.

Examples of the rare earth oxysulfide include a gadolinium oxysulfide ($Gd_2O_2S$), an yttrium oxysulfide ($Y_2O_2S$), a rutetium oxysulfide ($Lu_2O_2S$), and so on. The gadolinium oxysulfide has a high X-ray absorption coefficient, and thus can obtain a high optical output. Further, the rare earth oxysulfide contains, as an activator, one or two or more elements selected from Pr, Ce, Yb, Eu, and Tb.

As the gadolinium oxysulfide, for example, a gadolinium oxysulfide expressed by a composition satisfying the following general formula can be cited.

$$\text{General formula: } (Gd_{1-a-b}Pr_aM_b)_2O_2S \tag{1}$$

(where M is one or two or more elements selected from Ce, Yb, Eu, and Tb, a is a number satisfying $0.0001 \leq a \leq 0.01$, and b is a number satisfying $0 \leq b \leq 0.005$).

The M element in the general formula (1) is a coactivator, and has an effect of controlling an afterglow property and the like. Ce is an element effective for achieving a short afterglow. When the M element is contained, b in the above-described general formula (1) is more preferred to be a number satisfying $0.00001 \leq b \leq 0.005$. A part of Gd may be replaced with one or two or more elements selected from Y, La, and Lu.

The rare earth oxysulfide sintered body is manufactured by cutting out a portion of an ingot (large sintered body), for example. Therefore, when the ingot has a composition deviation, the optical output of the rare earth oxysulfide sintered body decreases and sensitivity of a scintillator array decreases in some cases. One of the reasons for composition deviation is that oxide and sulfide that are different from the rare earth oxysulfide remain in the sintered body. Therefore, the ceramic scintillator including the rare earth oxysulfide sintered body preferably includes few oxide regions containing oxide different from the rare earth oxysulfide and few sulfide regions containing sulfide different from the rare earth oxysulfide, or includes no oxide regions or sulfide regions.

The oxide has at least one of a rare earth oxide containing the same one or more elements as the rare earth elements of the rare earth oxysulfide and an impurity metal oxide, for example. The sulfide has at least one of a rare earth oxide containing the same one or more elements as the rare earth elements of the rare earth oxysulfide and an impurity metal oxide, for example.

When the rare earth oxysulfide sintered body 1a has the oxide regions and the sulfide regions, the oxide regions and the sulfide regions preferably have a major axis of 100 μm or less in an arbitrary cross-sectional structure of the rare earth oxysulfide sintered body 1a. When the major axis of each of the oxide regions and the sulfide regions exceeds 100 μm, the optical output decreases. The major axis of each of the oxide regions and the sulfide regions is preferred to be 30 μm or less, and more preferred to be 0 μm (a state where the oxide regions and the sulfide regions do not exist).

The oxide region and the sulfide region contain one or two or more elements selected from an alkali metal element, an alkaline earth metal element, and iron, for example. The oxide region and the sulfide region preferably contain one or two or more selected from Na (sodium), Ca (calcium), and Fe (iron). Na, Ca, and Fe are, as impurities, easily mixed in a phosphor or during a manufacturing process. In the case of containing the above-described impurities, these impurities are made to exist as small oxides or sulfides, thereby making it possible to reduce the effect on emission characteristics. Sodium oxide ($Na_2O$) is white, and sodium sulfide ($Na_2S$) is colorless. Further, calcium oxide (CaO) is white or blue-white. Further, calcium sulfide (CaS) is white. Iron oxide ($Fe_2O_3$) is red. In iron sulfide, $Fe_2S_3$ or FeS is black, and $FeS_2$ is gold.

Since the sodium oxide, the sodium sulfide, the calcium oxide, and the calcium sulfide are mainly white or colorless, the effect on emission characteristics is relatively low. Therefore, Na or Ca, which is easily mixed in as an impurity, is made to exist as the oxide or sulfide, thereby making it possible to reduce the effect of the rare earth oxysulfide sintered body on emission characteristics.

The iron oxide is red, and the iron sulfide is black or gold. The color of iron oxide or iron sulfide is dark, and thus the iron oxide and the iron sulfide are preferred to be as small as possible. An oxide or a sulfide of sodium or calcium preferably exists in the vicinity of the iron oxide or the iron sulfide. The sodium oxide, the sodium sulfide, the calcium oxide, and the calcium sulfide are mainly white or colorless. They are made to exist in the vicinity of the iron oxide or the iron sulfide, thereby making it possible to lighten the color of a colored region, which is red or the like. As a result, even though the oxide regions or the sulfide regions exist, it is possible to prevent a decrease in emission characteristics of the rare earth oxysulfide sintered body.

The vicinity of the iron oxide or the iron sulfide preferably falls within a range of 100 μm or less and further preferably falls within a range of 50 μm or less from the iron oxide or the iron sulfide. Whether or not it exists in the vicinity is confirmed by performing a semiquantitative analysis using an electron probe microanalyzer (EPMA) with a measuring spot diameter set to 100 μm or less, for example. It can be said that as long as Fe, Ca, Na, O, and S are detected in the measuring spot diameter, it is in a state where the iron oxide or the iron sulfide exists in the vicinity of one or more of the sodium oxide, the sodium sulfide, the calcium oxide, and the calcium sulfide. Further, using a transmission electron microscope (TEM) as necessary makes it possible to measure that each element turns into an oxide or a sulfide. Decreasing the measuring spot diameter of the EPMA makes it possible to measure how close to the vicinity it exists.

As long as a plurality of the oxide regions and a plurality of the sulfide regions exist even though the major axis of each of the oxide regions and the sulfide regions is 100 μm or less, the optical output decreases easily. Further, the chromaticity confirmation using a color meter has difficulty in detecting minute oxide regions and sulfide regions. The minimum measuring range of the diameter by a general color meter is about 2 mm or more and 8 mm or less. With the diameter of 2 mm or more and 8 mm or less, a measurement area is 3.14 mm² or more and 50.24 mm² or less. Even if a minute foreign matter having a major axis of 100 μm or less exists in this range, the range is recognized as an appropriate range in terms of the chromaticity.

In the ceramic scintillator according to the embodiment, the sum of the number of oxide regions and the number of sulfide regions, which exist in a unit area of 500 μm×500 μm in an arbitrary cross-sectional structure of the rare earth oxysulfide sintered body 1a, is five or less (including zero).

The cross-sectional structure is observed by a scanning electron microscope (SEM), for example. An SEM photograph is a composition image with a magnification of 100 times or more. A comparison between the oxide region, the sulfide region, and a rare earth oxysulfide region is made to reveal that in the above-described composition image, they are different in contrast. The oxide region and the sulfide region are shown deeper and darker in color than the rare earth oxysulfide region containing the rare earth oxysulfide. In the SEM composition image, as an atomic number is larger, a color becomes brighter, and thus Fe (atomic number 26), Na, (atomic number 11), and Ca (atomic number 20), which are impurities, are smaller in atomic number than Gd (atomic number 64), which is a main component, and thus are seen deeper and darker. Therefore, it is easy to distinguish the rare earth oxysulfide region from the oxide region and the sulfide region. Further, the EPMA may be used in combination as necessary.

Examples of the rare earth oxide include (a) a rare earth oxide remaining in a rare earth oxysulfide phosphor powder during a sintering process, (b) a rare earth oxide being a resolvent of the rare earth oxysulfide phosphor powder during the sintering process, (c) a rare earth oxide being a reactant of the rare earth oxysulfide sintered body in a heat treatment (strain relief heat treatment or the like) and oxygen in a heat treatment atmosphere, and so on. When the rare earth oxysulfide sintered body is $Gd_2O_2S$, the rare earth oxide is $Gd_2O_3$.

Examples of the rare earth sulfide include (d) a rare earth sulfide remaining in the rare earth oxysulfide phosphor powder during the sintering process, (e) a rare earth sulfide being a resolvent of the rare earth oxysulfide phosphor powder during the sintering process, and so on. When the rare earth oxysulfide sintered body is $Gd_2O_2S$, the rare earth sulfide is GdS.

Examples of the impurity metal oxide or the impurity metal sulfide include (f) an impurity metal oxide or an impurity metal sulfide contained in the rare earth oxysulfide phosphor powder, (g) an impurity metal oxide or an impurity metal sulfide to be mixed in during the manufacturing process, and so on.

The impurity metal oxide or the impurity metal sulfide contains one or two or more elements selected from an alkali metal element, an alkaline earth metal element, and iron, for example. As the alkali metal element, for example, Na (sodium) can be cited. As the alkaline earth metal element, for example, Ca (calcium) can be cited. The impurity metal oxide or the impurity metal sulfide may contain, for example, Cr (chromium) and the like as an impurity metal.

As another method of reducing the rare earth oxides and the rare earth sulfides in the rare earth oxysulfide sintered body, there can be cited a method in which a heat treatment is performed at a temperature of 1200° C. or more and 1600° C. or less in an inert gas atmosphere containing oxygen and sulfur to prevent whitening of a sintered body surface and completely remove internal coloring, for example. The above-described treatment method makes it possible to manufacture a scintillator having intended chromaticity coordinates (x, y) by measurement by a color meter. Therefore, it is possible to reduce oxygen deficiency and sulfur deficiency.

In the above-described method, however, the rare earth oxysulfide sintered body is treated by the reaction of oxygen gas and sulfur gas. Therefore, the case when the rare earth oxysulfide sintered body is large in size has difficulty in reducing the metal oxides even to the inside of the sintered body. Therefore, it is necessary to cut out a small sintered body having a volume of 1 mm$^3$ or less from a large sintered body (ingot) and confirm whether or not the metal oxide and the like remain therein. That is, the above-described treatment method is poor in mass productivity.

When there are a large number of samples when a sintered body cut out to be 1 mm$^3$ or less in volume beforehand is heat-treated in an inert gas atmosphere containing oxygen and sulfur, heat conductivity to the sample varies between a lower side and an upper side of a baking container, or between an outer side and an inner side of a baking container. When a heat treatment time is suited to the sample in which heat is not easily conducted, coarse grains are formed easily in the sample in which heat is conducted easily. In the ceramic scintillator including the rare earth oxysulfide sintered body having a volume of 1 mm$^3$ or less, the optical output is likely to vary when there are coarse grains. Further, when the heat treatment time is suited to the sample in which heat is conducted easily, the effect of reducing oxygen deficiency and sulfur deficiency in the sample in which heat is not easily conducted is insufficient.

The heat treatment in the inert gas atmosphere containing oxygen and sulfur is effective for the reduction in oxygen deficiency and sulfur deficiency. However, the heat treatment has a small effect of reducing adverse effects due to such impurity metal oxide and impurity metal sulfide as (f) and (g) described above. Further, when the oxides or the sulfides exist in the rare earth oxysulfide phosphor like (a) and (d) described above, a heat treatment for a long period of time is required in order to turn these into oxysulfides completely. Thus, coarse grains are formed easily. Further, in the above-described method, as long as the chromaticity coordinates (x, y) fall within a predetermined range, the scintillator is recognized as a good product, and thus there is a portion in which the above-described chromaticity coordinates and a remaining amount of the oxide regions and the sulfide regions do not correspond to each other.

At least some of the oxide regions and the sulfide regions preferably exist at a grain boundary between rare earth oxysulfide crystal grains, and further the oxide regions and the sulfide regions all preferably exist at a grain boundary between rare earth oxysulfide crystal grains. The oxide regions and the sulfide regions are made to exist at the grain boundary between the rare earth oxysulfide crystal grains, thereby enabling suppression of a decrease in emission characteristics of the rare earth oxysulfide crystal grains themselves. That the oxide region and sulfide region exist inside the rare earth oxysulfide crystal grain means that a state where impurities such as Fe, Na, and Ca are solid-dissolved in the rare earth oxysulfide crystal grain is made. When the impurity is solid-dissolved in the rare earth oxysulfide crystal grain, the emission characteristics of the rare earth oxysulfide crystal grain sometimes decrease. Therefore, the oxide regions and the sulfide regions preferably exist at the grain boundary between the rare earth oxysulfide crystal grains.

In the rare earth oxysulfide sintered body, an average crystal grain diameter of the rare earth oxysulfide crystal grains is preferred to be 5 µm or more and 30 µm or less. When the average crystal grain diameter is less than 5 µm, the number of grain boundaries between the rare earth oxysulfide crystal grains is large. Therefore, the number of oxide regions and sulfide regions existing at the grain boundary increases. When the average crystal grain diameter exceeds 30 µm, the grain boundary between the rare earth oxysulfide crystal grains is large. Therefore, the oxide regions and the sulfide regions existing at the grain boundary are likely to be large. The average crystal grain diameter of the rare earth oxysulfide crystal grains is preferred to be 7 µm or more and 20 µm or less.

In order to prevent the grain boundary between the rare earth oxysulfide crystal grains from increasing, the maximum diameter of the rare earth oxysulfide crystal grains is preferred to be 50 µm or less. As long as crystal grains having the maximum diameter of greater than 50 µm exist even though the average crystal grain diameter is 5 µm or more and 30 µm or less, the grain boundary between the rare earth oxysulfide crystal grains is likely to be large. The maximum diameter of the rare earth oxysulfide crystal grains is more preferred to be 35 µm or less.

The average crystal grain diameter of the rare earth oxysulfide crystal grains is defined by a measurement result obtained by a linear density method, for example. Specifically, a macrophotograph (SEM photograph) of a unit area of 500 μm×500 μm of an arbitrary cross-section of the rare earth oxysulfide sintered body is taken. A straight line having a length of 500 μm is drawn on the macrophotograph. Next, the number of rare earth oxysulfide crystal grains existing on the drawn straight line is counted. An average value is found by (the number of rare earth oxysulfide crystal grains/500 μm). The same operation is performed on each of five arbitrary straight lines. An average value of crystal grain diameters of rare earth oxysulfide crystal grains on the five arbitrary lines is the average crystal grain diameter.

The scintillator having the above-described rare earth oxysulfide sintered body exhibits excellent emission characteristics even when the volume is 1 mm³ or less. Further, in the ceramic scintillator according to the embodiment, the oxide regions and the sulfide regions are reduced in number, and thus the volume can be 0.72 mm³ or less.

Next, there will be explained a manufacturing method example of the scintillator according to the embodiment. A manufacturing method of the scintillator according to the embodiment is not limited in particular as long as this method can minimize the oxide regions and the sulfide regions. The following method can be cited as a method for efficiently obtaining the scintillator.

A rare earth oxysulfide powder is prepared. The rare earth oxysulfide powder is a phosphor powder. An average particle diameter of the rare earth oxysulfide powder is preferred to be 10 μm or less, and further preferred to be 5 μm or less. When the average particle diameter of the rare earth oxysulfide powder exceeds 10 μm, the crystal grains of the rare earth oxysulfide sintered body are large. When the crystal grains are too large, the grain boundary is likely to be large. Therefore, the oxide regions and the sulfide regions existing at the grain boundary are likely to be large.

Next, a water-washing process is performed on the rare earth oxysulfide powder. For production of the rare earth oxysulfide powder, flux is used in order to accelerate reaction of the rare earth oxysulfide powder and a sulphidizing agent. As the flux, for example, $A_3PO_4$, $A_2CO_3$, or the like is used. A of $A_3PO_4$ or $A_2CO_3$ is at least one element selected from Li, Na, K, Rb, and Cs. When the flux is used, the A element is likely to remain in the rare earth oxysulfide powder. The A element is a component soluble in water as an ion. Therefore, it is effective to perform the water-washing process. The water-washing process is effective also for removal of impurities to be mixed in inevitably during the manufacturing process.

In the water-washing process, separating impurities in the rare earth oxysulfide powder, or performing the water-washing process itself in a clean room is effective for removal of impurities. After the water-washing process, letting the water-washed rare earth oxysulfide powder pass through a mesh product to remove solid matters therefrom is effective for removal of impurities.

Next, a process of heat treating the rare earth oxysulfide powder in an inert gas atmosphere containing oxygen and sulfur is preferably performed. The heat treatment in the inert gas atmosphere containing oxygen and sulfur makes it possible to reduce oxide regions and sulfide regions in the rare earth oxysulfide powder. In the ceramic scintillator according to the embodiment, the major axis of the oxide regions and the sulfide regions is made minute, which is 100 μm or less (including zero). In order to achieve the above, it is necessary to sufficiently reduce the oxide regions and the sulfide regions in the rare earth oxysulfide powder itself to be a raw material powder.

The oxygen in the inert gas atmosphere containing oxygen and sulfur is not limited to oxygen contained in an oxygen gas, for example, and oxygen contained in the atmosphere and so on can be cited. As the sulfur, for example, a $SO_X$ gas and so on can be cited. The $SO_X$ gas contains sulfur and oxygen as its constituent, thus making it possible to reduce the oxide regions and the sulfide regions. As the $SO_X$ gas, a $SO_2$ gas, a $SO_3$ gas and so on can be cited.

A temperature of the heat treatment (first) in the inert gas atmosphere containing oxygen and sulfur is preferred to be 700° C. or more and 1350° C. or less. The heat treatment is intended for the rare earth oxysulfide powder, and thus can be performed at a temperature lower than ever before. A heat treatment time is preferred to be 0.5 hours or more and 30 hours or less.

The above-described heat treatment is preferably performed while stirring the inert gas atmosphere containing oxygen and sulfur. As being intended for the powder, the heat treatment process is performed while stirring the atmosphere gas, and thereby the atmosphere gas easily comes into contact with each of the rare earth oxysulfide powders. This makes it possible to reduce the oxide regions and the sulfide regions in the rare earth oxysulfide powder. Further, examples of the method of stirring the atmosphere gas include a method of stirring the atmosphere gas in a heat treatment container, a method of stirring the atmosphere gas while flowing the atmosphere gas, a method of stirring the atmosphere gas while stirring the rare earth oxysulfide powder, and so on.

A heating rate up to the heat treatment temperature in the inert gas atmosphere containing oxygen and sulfur is preferred to be 100° C./minute or less. Setting the heating rate to 100° C./minute or less makes it easier for the oxide regions and the sulfide regions in the rare earth oxysulfide powder to react with the rare earth oxysulfide.

Although the explanation is conducted in the order of the water-washing process and the heat treatment process, the water-washing process may be performed after the heat treatment process, or the water-washing process and the heat treatment process may be alternately performed repeatedly.

Next, a molding process is performed. In the molding process, the rare earth oxysulfide powder is molded. As a molding method, for example, metal mold pressing, rubber pressing, and so on can be cited. A molded body may be enclosed in a Ta capsule. The molding process is preferably performed in a clean room in order to remove impurities. Further, in the molding process, impurities attached to use materials such as a metal mold press, a rubber press, and a Ta capsule to be used may be removed before the use materials are used.

Next, a sintering process is performed. A sintering method is preferred to be, for example, hot pressing or a hot isostatic pressing (HIP) method. In the sintering process, preferably, for example, a temperature is set to 1400° C. or more and 1600° C. or less, a pressure is set to 98 MPa or more, and holding is performed for one hour or more and 10 hours or less. Setting such conditions makes it possible to obtain a rare earth oxysulfide sintered body having a relative density of 99.5% or more, for example.

When the heat treatment temperature is less than 1400° C., the sintered body is not densified. When the heat treatment temperature exceeds 1600° C., the oxide region and the sulfide region are formed easily.

When the pressure is less than 98 MPa, the sintered body is not densified. In order to reduce the oxide regions and the sulfide regions, it is preferred not use a sintering aid. Therefore, the pressure is preferred to be 120 MPa or more.

When the sintering time is less than one hour, the sintered body is not densified. When the sintering time exceeds 10 hours, the oxide region and the sulfide region are formed easily. The sintering time is preferred to be two hours or more and seven hours or less.

The second heat treatment in the inert gas atmosphere containing oxygen and sulfur is preferably performed on a sintered body obtained after the sintering process. By this heat treatment, the oxide regions or the sulfide regions formed in the sintering process can be reduced.

A temperature of the second heat treatment process is preferred to be 700° C. or more and 1350° C. or less. A heating rate of the second heat treatment process is preferred to be 50° C./minute or less. Slow heating can make the oxide regions or the sulfide regions react with the rare earth oxysulfide homogeneously. A heat treatment time of the second heat treatment process is preferred to be 1 hour or more and 40 hours or less, and further preferred to be two hours or more and 20 hours or less.

In this manner, the first heat treatment is performed on the rare earth oxysulfide powder, and then the second heat treatment is performed on the rare earth oxysulfide sintered body, thereby making it possible to reduce the oxide regions and the sulfide regions.

The above-described manufacturing method enables the major axis of the oxide regions and the sulfide regions to be 100 µm or less (including zero) and enables the number of oxide regions and sulfide regions to be five or less (including zero) per a unit area of 500 µm×500 µm even in a rare earth oxysulfide sintered body ingot of 1 mm or more in width, 1 mm or more in thickness, and 20 mm or more in length, for example. Therefore, it is possible to cut out a sintered body having a volume of 1 mm$^3$ or less from the rare earth oxysulfide sintered body ingot.

The ceramic scintillator according to the embodiment is suitable for a ceramic scintillator array. The ceramic scintillator array preferably includes a plurality of ceramic scintillators integrated with a reflection layer interposed therebetween.

Figure 2:
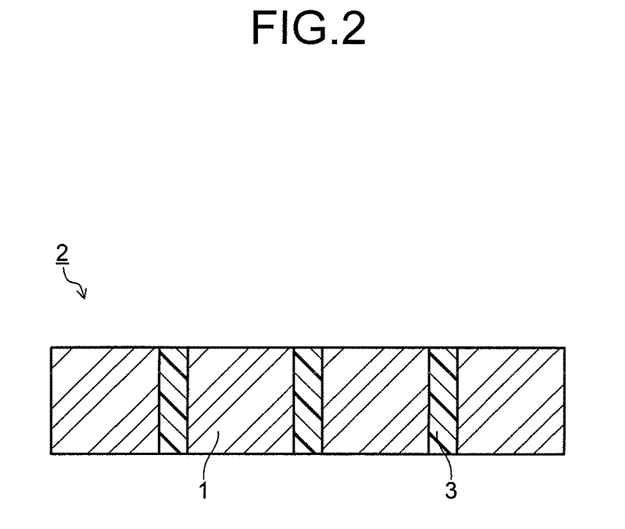
FIG. 2 is a schematic view illustrating a ceramic scintillator array according to an embodiment.
Figure 3:
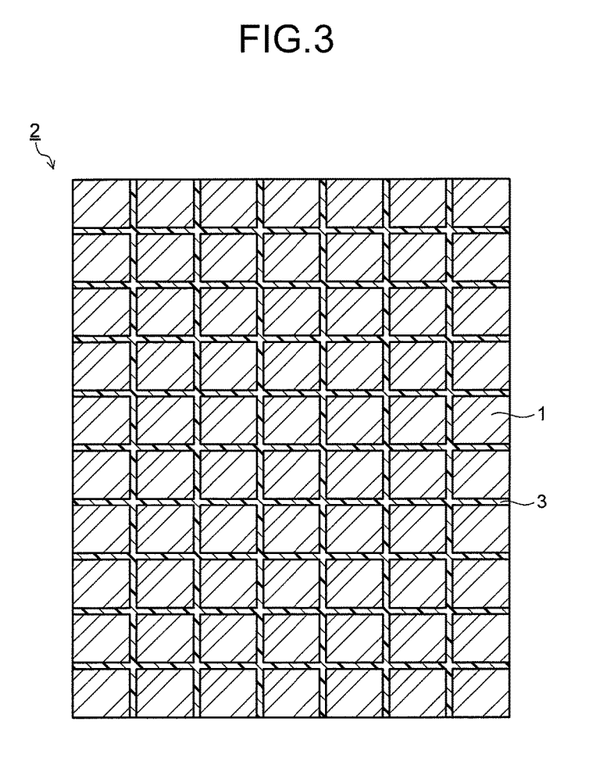
FIG. 3 is another schematic view illustrating the ceramic scintillator array according to the embodiment.

FIG. 2 and FIG. 3 are schematic views each illustrating a scintillator array. FIG. 2 is a side view of the ceramic scintillator array, and FIG. 3 is a top view of the ceramic scintillator array. A ceramic scintillator array 2 illustrated in FIG. 2 and FIG. 3 includes a plurality of the ceramic scintillators 1 and a reflection layer 3 provided between the plurality of the ceramic scintillators 1.

The reflection layer 3 contains a mixture of, for example, reflective particles such as $TiO_2$ or $Al_2O_3$ and resin. The reflection layer 3 may have a structure having a reflection film provided on a side surface of the ceramic scintillator 1 by using sputtering or the like. Further, the reflection layer 3 may also have a structure having a metal foil and resin layers provided on both surfaces of the metal foil. The reflection layer 3 reflects at least some of electromagnetic waves.

In the ceramic scintillator array 2, the reflection layer 3 can be reduced in thickness to 100 µm or less, and further to 50 µm or less because the ceramic scintillator 1 is miniaturized to be 1 mm$^3$ or less in volume.

Figure 4:
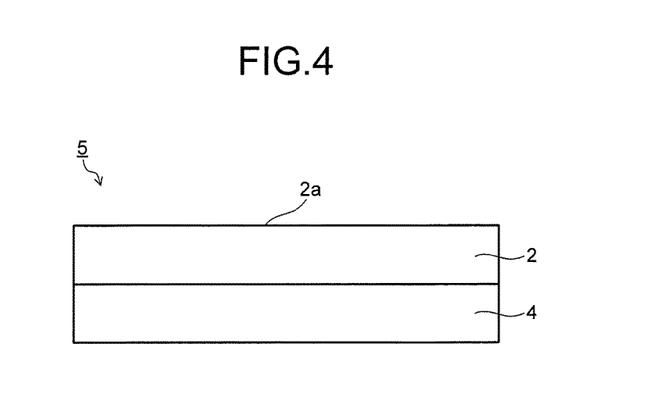
FIG. 4 is a schematic view illustrating a radiation detector according to an embodiment.

Next, there is explained a radiation detector. FIG. 4 is a view illustrating a radiation detector. A radiation detector 5 illustrated in FIG. 4 includes the ceramic scintillator array 2 and a photoelectric conversion element 4. The ceramic scintillator array 2 has an X-ray incident surface 2a. The ceramic scintillator array 2 may have a surface reflection layer on the X-ray incident surface 2a. The surface reflection layer may be provided not only on the X-ray incident surface 2a of the ceramic scintillator array 2 but also on a mounting surface of the photoelectric conversion element 4. Further, the surface reflection layer may be provided on both the X-ray incident surface 2a of the ceramic scintillator array 2 and the mounting surface of the photoelectric conversion element 4.

Providing the surface reflection layer on the ceramic scintillator array 2 makes it possible to further improve reflection efficiency of visible light emitted from the ceramic scintillators 1 and increase an optical output of the ceramic scintillator array 2.

As the surface reflection layer, for example, a mixture of reflective particles and a transparent resin, a lacquer-based coating material or the like is used. The mixture of reflective particles and a transparent resin preferably has a dispersion state of the reflective particles as in the reflection layer 3. A thickness of the surface reflection layer is preferred to be 50 µm or more and 250 µm or less. When the thickness of the surface reflection layer is less than 50 µm, it is not possible to obtain a sufficient improvement effect of the reflection efficiency. When the thickness of the surface reflection layer exceeds 250 µm, the surface reflection layer decreases in the amount of X-rays transmitted therethrough to decrease in detection sensitivity.

The photoelectric conversion element 4 is integrally mounted on a surface opposite to the X-ray incident surface 2a of the ceramic scintillator array 2. As the photoelectric conversion element 4, for example, a photodiode is used. The photoelectric conversion element 4 is disposed at a position corresponding to the ceramic scintillators 1 constituting the ceramic scintillator array 2.

Figure 5:
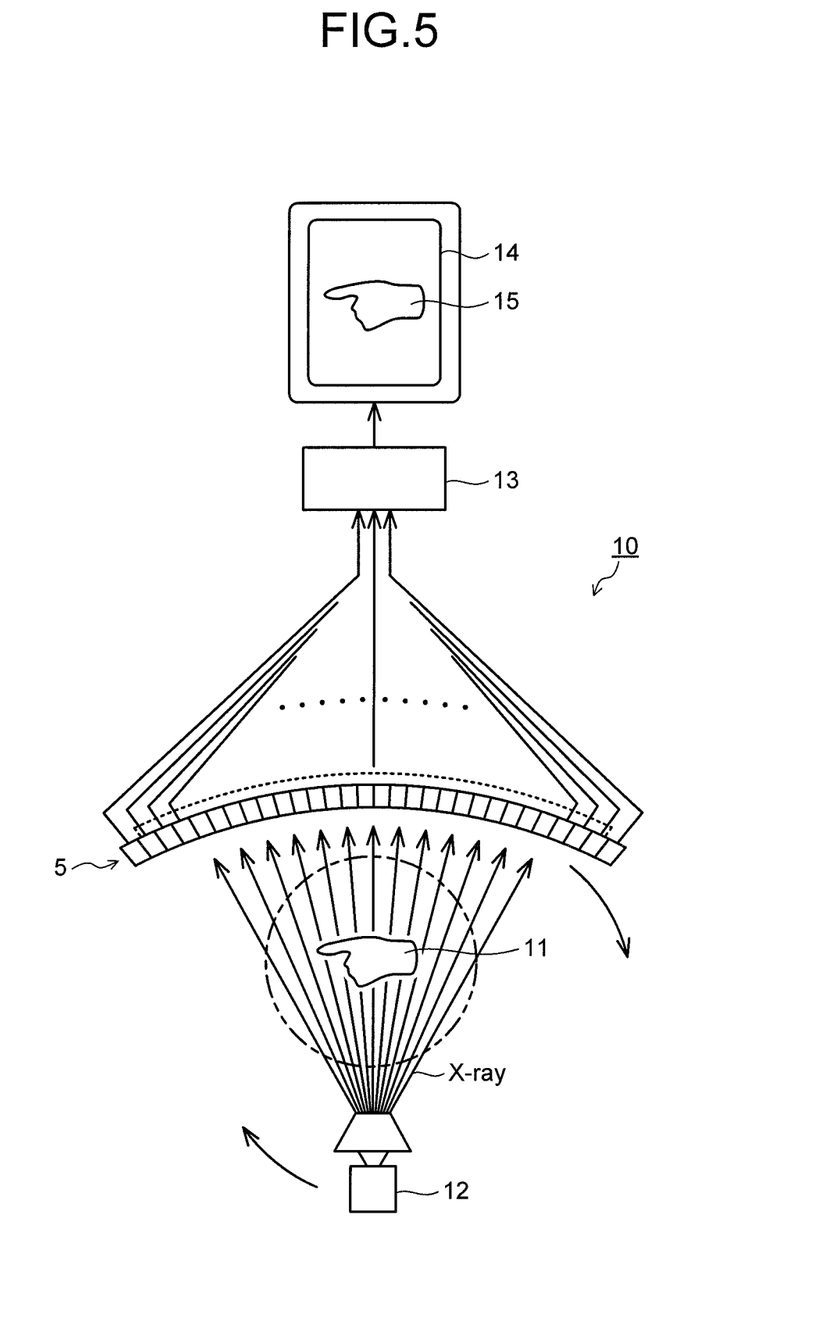
FIG. 5 is a schematic view illustrating a radiation examination device according to an embodiment.

Next, there is explained an X-ray CT device as one example of a radiation examination device. FIG. 5 is a view illustrating a configuration example of an X-ray CT device. An X-ray CT device 10 illustrated in FIG. 5 includes at least a radiation detector 5 and an X-ray tube 12.

The radiation detector 5 is pasted to an inner wall surface of a cylinder in which a photographing region of a specimen 11 is to be laid out. On the X-ray incident surface side of the radiation detector 5, a not-illustrated collimator is provided. As the radiation detector 5, for example, the radiation detector 5 or the like illustrated in FIG. 4 or the like can be applied.

The X-ray tube 12 emits X-rays. The X-ray tube 12 is provided almost at the center of an arc of the cylinder to which the radiation detector 5 is pasted. Between the radiation detector 5 and the X-ray tube 12, the specimen 11 is disposed.

The radiation detector 5 and the X-ray tube 12 are configured to rotate around the specimen 11 while photographing with the X-rays. Therefore, pieces of image information of the specimen 11 at different angles can be three-dimensionally collected. Signals obtained by the X-ray photographing (electric signals converted by the photoelectric conversion element) are processed by a computer 13 and displayed on a display 14 as a specimen image 15.

The specimen image 15 is, for example, a tomogram of the specimen 11. Using the ceramic scintillator array 2 including the two-dimensionally arranged ceramic scintillators 1 illustrated in FIG. 3 makes it possible to configure a multi-tomogram type X-ray CT device 10. In this case, a plurality of tomograms of the specimen 11 can be simultaneously photographed to, for example, three-dimensionally draw photographing results.

As described above, the ceramic scintillator array 2 according to the embodiment can obtain an excellent optical output because of its high reflection efficiency for the visible light emitted from the ceramic scintillators 1 based on the configuration and the like of the reflection layer 3. Using the radiation detector 5 having the ceramic scintillator array 2 as above makes it possible to shorten the photographing time by the X-ray CT device 10. As a result, it is possible to shorten the radiation exposure time of the specimen 11 and achieve reduced radiation exposure. The X-ray examination device (X-ray CT device 10) according to the embodiment is applicable not only to the X-ray examination for medical diagnosis of a human body but also to the X-ray examination for animals, the X-ray examination for industrial usage and so on.

The X-ray examination device according to the embodiment can obtain a high definition image because of using the ceramic scintillators each having a volume of 1 mm$^3$ or less. Further, the scintillators are each miniaturized to be 1 mm$^3$ or less in volume and then the oxide regions and the sulfide regions are minimized, resulting in excellent emission characteristics of each of the scintillators. Therefore, the characteristics of the scintillator array in which a plurality of the scintillators according to the embodiment are used are also excellent.

EXAMPLE

Examples 1 to 8, Comparative Examples 1 to 2

As a gadolinium oxysulfide powder, a material having a composition expressed by $(Gd_{0.999},Pr_{0.001})_2O_{2\pm0.01}S_{1\pm0.01}$ was prepared. Next, as illustrated in Table 1, a washing process and a heat treatment process (first time) were performed on the powder. In the washing process, the material was washed with pure water.

TABLE 1

| | Average Particle Diameter (μm) | Washing Process | Heat Treatment Process | | |
|---|---|---|---|---|---|
| | | | Atmosphere | Temperature × Time (° C. × Time) | Heating Rate (° C./min) |
| Example 1 | 5 | Performed | SO$_2$Gas + Atmosphere | 700 × 5 | 80 |
| Example 2 | 7 | Performed | SO$_2$Gas + Atmosphere | 800 × 5 | 50 |
| Example 3 | 10 | Performed | SO$_2$Gas + Atmosphere | 1000 × 2 | 35 |
| Example 4 | 12 | Performed | SO$_2$Gas + Atmosphere | 1100 × 2 | 30 |
| Example 5 | 15 | None | SO$_2$Gas + Atmosphere | 1200 × 2 | 20 |
| Example 6 | 8 | Performed | SO$_2$Gas + Atmosphere | 1150 × 3 | 35 |
| Example 7 | 10 | Performed | SO$_2$Gas + Atmosphere | 1200 × 3 | 40 |
| Example 8 | 6 | Performed | SO$_2$Gas + Atmosphere | 1100 × 3 | 40 |
| Comparative Example 1 | 10 | None | None | None | None |
| Comparative Example 2 | 10 | Performed | None | None | None |

The gadolinium oxysulfide powders according to Examples and Comparative examples were each used, and a molding process and a sintering process were performed thereon. In the molding process, the gadolinium oxysulfide powder was temporarily molded by rubber pressing to be enclosed in a Ta capsule. A HIP process at 1500° C. and 150 MPa and for five hours was performed on a molded body enclosed in the Ta capsule. By this process, a sintered body ingot of 2 mm in thickness×2 mm in width×30 mm in length was fabricated. Next, a heat treatment process (second time) illustrated in Table 2 was performed on each of the sintered body ingots each from which the Ta capsule was removed.

TABLE 2

| | Heat Treatment Process (Second Time) | | |
|---|---|---|---|
| | Atmosphere | Temperature × Time (° C. × Time) | Heating Rate (° C./min) |
| Example 1 | SO$_2$Gas + Atmosphere | 1200 × 12 | 50 |
| Example 2 | SO$_2$Gas + Atmosphere | 1000 × 15 | 40 |
| Example 3 | SO$_2$Gas + Atmosphere | 900 × 20 | 30 |
| Example 4 | SO$_2$Gas + Atmosphere | 1300 × 5 | 20 |
| Example 5 | SO$_2$Gas + Atmosphere | 1100 × 10 | 30 |
| Example 6 | SO$_2$Gas + Atmosphere | 1150 × 10 | 35 |
| Example 7 | SO$_2$Gas + Atmosphere | 1200 × 10 | 40 |
| Example 8 | SO$_2$Gas + Atmosphere | 1100 × 10 | 40 |
| Comparative Example 1 | SO$_2$Gas + Atmosphere | 1300 × 24 | 200 |
| Comparative Example 2 | SO$_2$Gas + Atmosphere | 1300 × 5 | 200 |

From each of the sintered body ingots, a sample of 0.7 mm in thickness×0.7 mm in width×0.8 mm in length was cut out and ceramic scintillators according to Examples and Comparative examples were fabricated therefrom. The average crystal grain diameter and the maximum diameter of gadolinium oxysulfide crystal grains of each of the ceramic scintillators were examined. Further, the major axis of oxide regions and sulfide regions and the number of oxide regions and sulfide regions per unit area were examined.

An arbitrary cross-section of each of the ceramic scintillators was observed by a SEM as measurement. Using a SEM composition image (3000 magnifications), the gadolinium oxysulfide crystal grains shown thereon were found by a linear density method. Further, the average crystal grain diameter of these was found. The longest diagonal line of the gadolinium oxysulfide crystal grains shown on the SEM composition image (3000 magnifications) was set as the maximum diameter of the major axis of the crystal grain.

Next, an EPMA analysis was performed on an arbitrary cross-section of each of the ceramic scintillators. A measuring spot of the EPMA was set to 100 μm and measurement was performed so that the unit area became 500 μm×500 μm in total. By this operation, the major axis of the oxide regions and the sulfide regions and the number of oxide regions and sulfide regions were found. Results of the above are illustrated in Table 3.

TABLE 3

| | Crystal Grain | | Oxide Region or Sulfide Region | |
|---|---|---|---|---|
| | Average Crystal Grain Diameter (μm) | Major Axis Maximum Diameter (μm) | Major Axis (μm) | Number (piece) |
| Example 1 | 7.2 | 15.2 | 23 | 3 |
| Example 2 | 13.5 | 20.7 | 15 | 2 |
| Example 3 | 17.1 | 24.1 | 8 | 2 |
| Example 4 | 19.6 | 27.1 | 0 | 0 |
| Example 5 | 21.7 | 29.7 | 30 | 2 |
| Example 6 | 11.3 | 14 | 0 | 0 |
| Example 7 | 14 | 16.7 | 10 | 1 |
| Example 8 | 10.8 | 13.4 | 5 | 1 |
| Comparative Example 1 | 15.2 | 20.9 | 125 | 10 |
| Comparative Example 2 | 13.6 | 18.2 | 140 | 14 |

As is clear from Table, in the ceramic scintillators according to Examples, the major axis of the oxide regions or the sulfide regions was 100 μm or less (including zero) and the number of oxide regions and sulfide regions was five or less (including zero) per a unit area of 500 μm×500 μm.

In the ceramic scintillators according to Examples and Comparative examples, at least one element selected from Fe, Na, and Ca was detected from the oxide regions and the sulfide regions. Further, the SEM composition image was photographed, and then a comparison between the oxide region and the sulfide region and a rare earth oxysulfide region was made to reveal that they are different in contrast and the oxide regions and the sulfide regions were seen deeper and darker in color than the rare earth oxysulfide region.

Next, ceramic scintillator arrays were fabricated using the ceramic scintillators according to Example and Comparative examples. As a reflection layer, an epoxy resin containing $TiO_2$ was prepared. A thickness of the reflection layer was set to 100 μm or 50 μm, and the ceramic scintillators were arranged in a matrix in a plane to fabricate a ceramic scintillator array.

An optical output of the ceramic scintillator array was measured. In the measurement of optical output, a scintillator array having the same size was fabricated of cadmium tungstate ($CdWO_4$). Further, the scintillator array was set in a radiation detector and a value of electric current to flow through a silicon photodiode when an X-ray having 120 kV and 200 mA was irradiated was found as an optical output. At this time, as a relative value when the optical output of the scintillator array using cadmium tungstate was set to 100, the optical output was found. Results of the above are illustrated in Table 4.

TABLE 4

| | Optical Output Relative Value | |
|---|---|---|
| | Reflection Layer Thickness 100 μm | Reflection Layer Thickness 50 μm |
| Example 1 | 210 | 211 |
| Example 2 | 220 | 225 |
| Example 3 | 225 | 228 |
| Example 4 | 235 | 240 |
| Example 5 | 215 | 221 |
| Example 6 | 233 | 238 |
| Example 7 | 217 | 219 |
| Example 8 | 219 | 224 |
| Comparative Example 1 | 195 | 190 |
| Comparative Example 2 | 190 | 187 |

As is clear also from Table, in each of the scintillator arrays according to Examples, the output improved. Each of the scintillator arrays according to Examples had few oxide regions and sulfide regions, thus being able to obtain excellent characteristics even when the thickness of the reflection layer was set to 100 μm or less, and further set to 50 μm or less. This reveals that the reflection layer can be reduced in thickness in the scintillator array according to the embodiment.

In the scintillator arrays according to Comparative examples, the major axis of the oxide regions or the sulfide regions exceeded 100 μm to be large and the number of oxide regions or sulfide regions per unit area was large, and thus it was not possible to confirm an improvement in optical output. This reveals that the ceramic scintillator array according to Comparative example is not necessary appropriate when the reflection layer is reduced in thickness.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions. Further, the above-described respective embodiments can be implemented in a manner to be combined mutually.

What is claimed is:

1. A scintillator, comprising:

a sintered body being 1 mm³ or less in volume and containing at least one rare earth oxysulfide selected from the group consisting of a gadolinium oxysulfide, an yttrium oxysulfide, and a rutetium oxysulfide;

wherein, in a composition image obtained by observing a cross-section of the sintered body under a scanning electron microscope, the sum of the number of oxide regions that contain at least one of a rare earth oxide different from the rare earth oxysulfide and an impurity metal oxide and the number of sulfide regions that contain at least one of a rare earth sulfide different from the rare earth oxysulfide and an impurity metal sulfide, which exist in a unit area of 500 μm×500 μm, is one or more and five or less, wherein each of the oxide regions and the sulfide regions has a major axis of 100 μm or less, wherein, in the composition image, the oxide region and the sulfide region are deeper and darker in color than a rare earth oxysulfide region containing the rare earth oxysulfide, wherein the rare earth oxide and the rare earth sulfide contain at least one element in common with rare earth elements contained in the rare earth oxysulfide, wherein the impurity metal oxide and the impurity metal sulfide contain at least one element selected from the group consisting of an alkali metal element, an alkaline earth metal element, and iron, wherein the sintered body has a plurality of rare earth oxysulfide crystal grains, and wherein at least some of the oxide regions and the sulfide regions exist at a grain boundary between the grains.

2. The scintillator according to claim 1, wherein the sintered body is 0.72 mm$^3$ or less in volume.

3. The scintillator according to claim 1, wherein a composition of the gadolinium oxysulfide is expressed by General formula: $(Gd_{1-a-b}Pr_a M_b)_2 O_2 S$    (1), where M is at least one element selected from the group consisting of Ce, Yb, Eu, and Tb, a is a number satisfying $0.0001 \leq a \leq 0.01$, and b is a number satisfying $0 \leq b < 0.005$.

4. The scintillator according to claim 1, wherein an average crystal grain diameter of the grains is 5 μm or more and 30 μm or less.

5. The scintillator according to claim 1, wherein a maximum diameter of the grains is 50 μm or less.

6. A scintillator array, comprising:
a plurality of scintillators including the scintillator according to claim 1; and
a reflection layer provided between a plurality of the scintillators.

7. A radiation detector, comprising:
the scintillator array according to claim 6, having an X-ray incident surface; and
a photoelectric conversion element provided on a surface opposite to the X-ray incident surface of the scintillator array.

8. The radiation detector according to claim 7, further comprising:
a surface reflection layer provided on at least one surface of the X-ray incident surface and the surface opposite thereto.

9. A radiation examination device comprising the radiation detector according to claim 7.

10. A method of manufacturing the scintillator according to claim 1, comprising the steps of:
washing a rare earth oxysulfide powder with water, the powder having an average particle diameter of 10 μm or less;
heating the powder at a temperature of 700 to 1350° C. for 0.5 to 30 hours in an inert gas atmosphere containing oxygen and sulfur;
molding the powder to form a molded body;
sintering the molded body in a Ta capsule at a temperature of 1400 to 1600° C. and at a pressure of 120 MPa or more for 2 to 7 hours, by a hot isostatic pressing method to form a sintered body; and
heating the sintered body at a temperature of 700 to 1350° C. for 2 to 20 hours in an inert gas atmosphere containing oxygen and sulfur.

\* \* \* \* \*